United States Patent
Yakabe et al.

(10) Patent No.: US 7,023,223 B2
(45) Date of Patent: *Apr. 4, 2006

(54) IMPEDANCE MEASURING CIRCUIT AND CAPACITANCE MEASURING CIRCUIT

(75) Inventors: Masami Yakabe, Tokyo (JP); Naoki Ikeuchi, Tokyo (JP); Toshiyuki Matsumoto, Tokyo (JP); Koichi Nakano, Hyogo (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/488,680

(22) PCT Filed: Sep. 6, 2002

(86) PCT No.: PCT/JP02/09136

§ 371 (c)(1),
(2), (4) Date: Sep. 24, 2004

(87) PCT Pub. No.: WO03/023419

PCT Pub. Date: Mar. 20, 2003

(65) Prior Publication Data

US 2005/0030046 A1    Feb. 10, 2005

(30) Foreign Application Priority Data

Sep. 6, 2001   (JP)   ............... 2001-269991

(51) Int. Cl.
*G01R 27/26* (2006.01)
(52) U.S. Cl. ............................ 324/686; 324/713
(58) Field of Classification Search ............ 324/158.1, 324/649, 684, 688, 690, 686, 713
See application file for complete search history.

(56) References Cited

U.S. PATENT DOCUMENTS

| | | | |
|---|---|---|---|
| 6,373,264 B1 * | 4/2002 | Matsumoto et al. | 324/667 |
| 6,756,790 B1 * | 6/2004 | Yakabe et al. | 324/649 |
| 6,825,649 B1 * | 11/2004 | Nakano | 324/126 |
| 6,828,806 B1 * | 12/2004 | Hirota et al. | 324/688 |

FOREIGN PATENT DOCUMENTS

DE      3007426 A1     9/1981

(Continued)

OTHER PUBLICATIONS

European Search report, by Moulara, G, prepared on Dec. 14, 2004, for application EP 02767920, at the European Patent Office located at The Hague, Neteherlands. No. of pp. - 2.

*Primary Examiner*—Walter Benson
(74) *Attorney, Agent, or Firm*—Finnegan, Henderson, Farabow, Garrett & Dunner, L.L.P.

(57) ABSTRACT

An electrostatic capacitance detection circuit 10 comprises an AC voltage generator 11, an operational amplifier 14 of which non-inverting input terminal is connected to specific potential (a ground in this example), an impedance converter 16, a resistance (R1) 12 connected between the AC voltage generator 11 and an inverting input terminal of the operational amplifier 14, a resistance (R2) 13 connected between the inverting input terminal of the operational amplifier 14 and an output terminal of the impedance converter 16, and an impedance element (a capacitor) 15 connected between an output terminal of the operational amplifier 14 and an input terminal of the impedance converter 16. A capacitor to be detected 17 is connected between the input terminal of the impedance converter 16 and the specific potential.

6 Claims, 6 Drawing Sheets

FOREIGN PATENT DOCUMENTS

| | | |
|---|---|---|
| DE | 3428699 A1 | 2/1986 |
| JP | 09-280806 | 10/1997 |
| JP | 2001-324520 | 11/2001 |
| JP | 2002-022785 | 1/2002 |
| JP | 2002-022786 | 1/2002 |
| JP | 2002-157671 | 5/2002 |
| WO | WO 99/38019 | 7/1999 |

* cited by examiner

IMPEDANCE MEASURING CIRCUIT AND CAPACITANCE MEASURING CIRCUIT

TECHNICAL FIELD

The present invention relates to a circuit that detects impedance, especially relates to the circuit that detects very small impedance with high accuracy.

BACKGROUND ART

Figure 1:
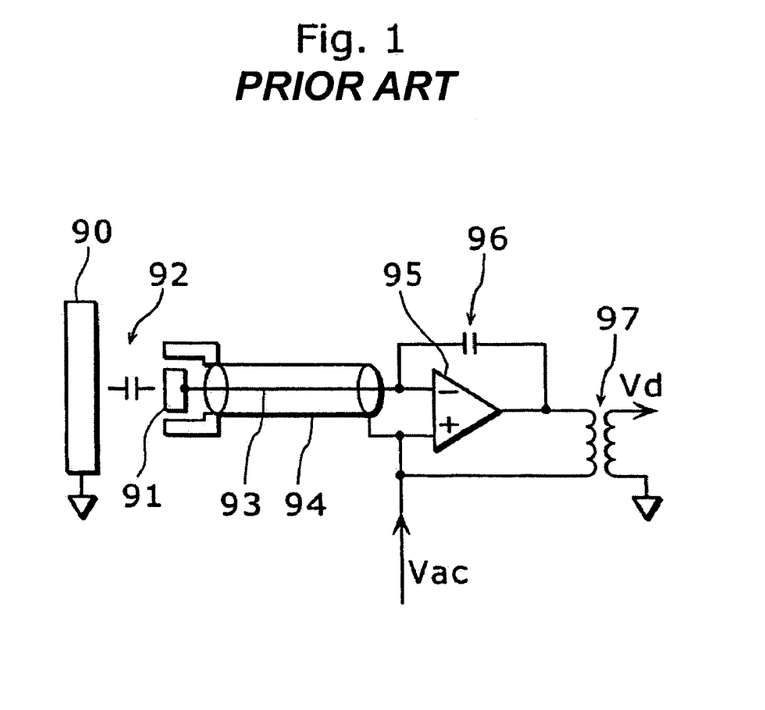
FIG. 1 is a circuit diagram showing a conventional electrostatic capacitance detection circuit.

As a prior art of an electrostatic capacitance detection circuit, that described in Japanese Laid-Open Patent Application H09-280806 gazette can be cited. FIG. 1 is a circuit diagram that shows this electrostatic capacitance detection circuit. In this detection circuit, a capacitive sensor 92 comprised of electrodes 90 and 91 is connected to an inverting input terminal of an operational amplifier 95 via a signal line 93. And a capacitor 96 is connected between an output terminal of this operational amplifier 95 and the said inverting input terminal, and further an AC voltage Vac is applied to a non-inverting input terminal. Also, the said signal line 93 is wrapped up by a shield line 94 and shielded electrically against disturbance noise. And this shield line 94 is connected to the non-inverting input terminal of the operational amplifier 95. Output voltage Vd is obtained from an output terminal of the said operational amplifier 95 via a transformer 97.

In this detection circuit, the inverting input terminal and the non-inverting input terminal of the operational amplifier 95 are in an imaginary short status, so that the signal line 93 connected to the inverting input terminal and the shield line 94 connected to the non-inverting input terminal have the almost same potential.

According to this kind of conventional art, when capacitance of the capacitive sensor 92 is big to some extend, it is indeed possible to obtain accurate output voltage Vd, which is not affected by the stray capacitance between the signal line 93 and the shield line 94. However, when very small capacitance, which equals to or is less than an order of several pF or fF (femtofarad), is detected, an error is increased.

Also, depending on a frequency of the AC voltage Vac applied, a subtle displacement of a phase and amplitude consequently arises between the voltage of the inverting input terminal and that of the non-inverting input terminal, which are in the imaginary short status, due to a tracking error in the operational amplifier 95, and thereby the detection error becomes bigger.

On the other hand, for lightweight and small audio communication devices represented by a mobile phone or the like, there has been a demand of a compact amplifier circuit that sensitively and faithfully transforms sounds detected by a capacitive sensor such as a capacitor microphone into an electric signal. If it is possible to accurately detect very small capacitance that equals to or is less than several pF or fF and/or its change, a high performance microphone that can detect sounds with a very high level of sensitivity and fidelity is realized, and thereby performance for picking up sounds by the audio communication devices such as a mobile phone will make rapid progress.

This invention is devised in view of the above-mentioned situation, and aims at providing a detection circuit of impedance including electrostatic, which is capable of accurately detecting very small capacitance, and suitable to detect capacitance of a capacitive sensor such as a capacitor microphone used for lightweight and compact audio communication devices.

DISCLOSURE OF INVENTION

In order to achieve above objectives, the electrostatic capacitance detection circuit according to the present invention is an impedance detection circuit that outputs a detection signal corresponding to impedance of an impedance element to be detected, comprising: an impedance converter of which input impedance is high and output impedance is low; a first capacitive impedance element; a first operational amplifier; a voltage generator that applies at least AC voltage or DC voltage to the first operational amplifier; and a signal output terminal that is connected to an output of the first operational amplifier, wherein an input terminal of the impedance converter is connected to one end of the impedance element to be detected and one end of the first impedance element, and the first impedance element and the impedance converter are included in a negative feedback loop of the first operational amplifier.

As a specific example, an impedance detection circuit is structured to comprise a voltage generator, an operational amplifier of which non-inverting input terminal is connected to specific potential, an impedance converter, a resistance connected between the voltage generator and an inverting input terminal of the operational amplifier, a resistance connected between the inverting input terminal of the operational amplifier and an output terminal of the impedance converter, and a first capacitive impedance element connected between an output terminal of the operational amplifier and an input terminal of the impedance converter. Impedance to be detected is connected between the input terminal of the impedance converter and the specific potential. The specific potential in the example here indicates either certain standard potential, specific DC potential, ground potential or a floating status, whichever suitable is selected according to a style of an embodiment.

According to the above structure, a certain voltage is applied to the impedance to be detected, most of electric current that flows through the impedance to be detected is further sent to the first impedance element, and then a signal corresponding to the impedance of the impedance to be detected is output from a signal output terminal.

In order to reduce noise mixed in the signal line that connects the impedance detection circuit and the impedance to be detected, and also reduce the stray capacitance between the signal line and the specific potential, it is preferable that the signal line for the impedance to be detected and the impedance detection circuit is as short as possible.

Also, as a type of the voltage generator, either AC or DC can be selected. Regarding characteristics of these types, the DC voltage generator can measure both absolute impedance and an amount changed in the impedance, whereas the AC voltage generator only detects the amount changed in the impedance. In the case of the DC voltage generator, size of its whole detection circuit becomes a little bigger since it requires an oscillator circuit or the like. But, in the case of the AC voltage generator, it can remain compact because it does not require that. Therefore, according to a purpose or a use, the most suitable one can be selected for the voltage generator of the present invention. In addition, a second impedance element can be located between the said first operational amplifier and the said voltage generator. Also, a resistance may be connected in parallel with the first impedance element.

Here, because the output signal from the said signal output terminal includes a signal corresponding to voltage generated by the voltage generator, a cancellation unit for canceling it can further be added to the said impedance detection circuit. An adding unit, a subtracting unit or the like can be given as an example of this cancellation unit. Especially, for a case that the impedance to be detected is capacitive, using a capacitor for the first impedance can realize a circuit that excels at a frequency characteristic.

BEST MODE FOR CARRYING OUT THE INVENTION

The following provides a detailed explanation of embodiments of the present invention with reference to diagrams.

(First Embodiment)

Figure 2:
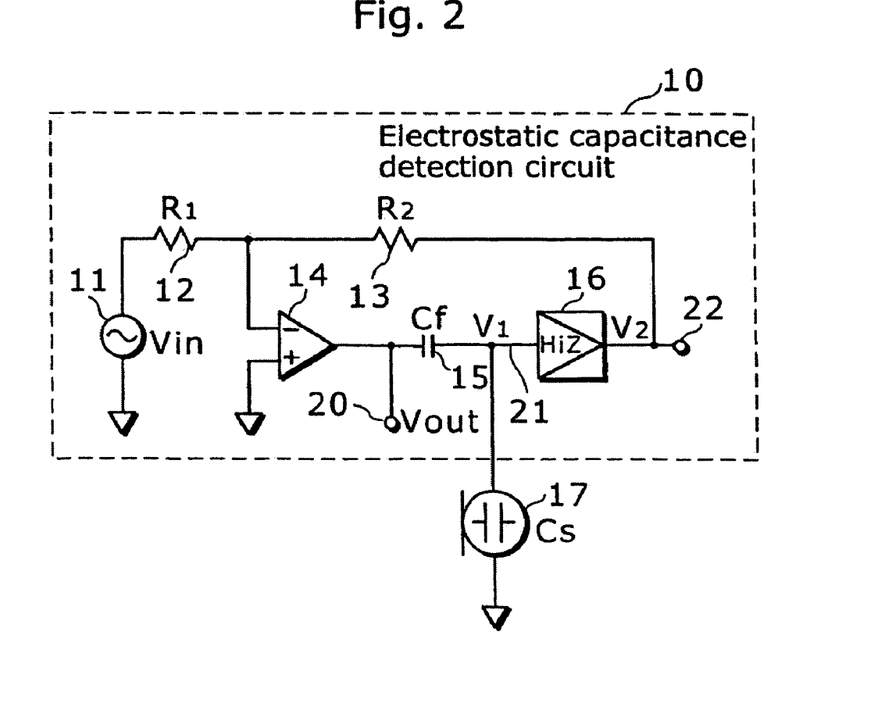
FIG. 2 is a circuit diagram of an electrostatic capacitance detection circuit as an impedance detection circuit according to a first embodiment of the present invention.

FIG. 2 is a circuit diagram of an impedance detection circuit according to a first embodiment of the present invention. In this diagram, an electrostatic capacitance detection circuit 10 as this impedance detection circuit is connected to a capacitor to be detected 17 as impedance to be detected that is a subject for detection (i.e. a capacitance type sensor that detects various types of physical quantities using a fluctuation in the electrostatic capacitance Cs such as a capacitor microphone in this example).

This electrostatic capacitance detection circuit 10 comprises an AC voltage generator 11 that generates AC voltage, a resistance (R1) 12, a resistance (R2) 13, an operational amplifier 14, an impedance element 15 (a capacitor with capacitance Cf in this example) and an impedance converter 16, and outputs a detection signal (voltage V out) corresponding to electrostatic capacitance of the capacitor 17 from a signal output terminal 20.

One end of the AC voltage generator 11 is connected to specific electrical potential (a ground in this example), and other end (an output terminal) of that generates specific AC voltage (voltage V in, angular frequency ω). The resistance (R1) 12 is connected between the output terminal of the AC voltage generator 11 and an inverting input terminal of the operational amplifier 14.

The operational amplifier 14 is a voltage amplifier with a high level of input impedance and an open loop gain, a non-inverting input terminal here is connected to specific potential (the ground in this example), and the non-inverting input terminal and the inverting input terminal are in an imaginary short status. In a negative feedback loop of this operational amplifier 14, which is from an output terminal to the inverting input terminal of the operational amplifier 14, the capacitor 15, the impedance converter 16 and the resistance (R2) 13 are connected in series in this order.

The impedance converter 16 is a voltage amplifier of which input impedance is extremely high, output impedance is extremely low, and voltage gain is A times. An input terminal 21 of this impedance converter 16 is connected to one end of the capacitor 17 via a signal line or an electric conductor such as a wiring patter on a printed circuit board, and other end of the capacitor 17 is connected to specific potential (the ground in this example). An output terminal of the operational amplifier 14 is connected to an output signal of this electrostatic capacitance detection circuit 10, i.e. the signal output terminal 20 for outputting a detection signal corresponding to the capacitance of the capacitor 17. In this patent document, a variable A indicated for the A times or the like shows any real number other than zero.

As for the connection between the capacitor 17 and the electrostatic capacitance detection circuit 10, it is preferable that an unshielded electric conductor, which is as short as possible, (such as a cable, a copper foil wiring pattern, a connection terminal) is used, so that it is possible to prevent any unnecessary stray capacitance from being added as a detection error, or a disturbance noise from being mixed. Moreover, to enhance a shield against the disturbance noise, it is preferable that a whole part of the capacitor 17 and the electrostatic capacitance detection circuit 10 is covered with a grounded shield material or put in a shield box if possible.

Actions of the electrostatic capacitance detection circuit 10 structured above are as follows.

Regarding an inverting amplification circuit comprising the resistance (R1) 12, the resistance (R2) 13 and the operational amplifier 14 and the like, both of the input terminals of the operational amplifier 14 are in the imaginary short status and in the same potential (e.g. 0 V), their impedance is extremely high, and no electric current flows through, so that the electric current passed through the resistance (R1) 12 becomes Vin/R1. Because all of the electric current is passed through the resistance (R2) 13, the following expression becomes effective when the output voltage of the impedance converter 16 is V2.

$$Vin/R1 = -V2/R2$$

When summarizing this, the output voltage V2 of the impedance converter 16 can be expressed by the following expression.

$$V2 = -(R2/R1) \cdot Vin \quad \text{(Expression 1)}$$

Also, because a voltage gain of the impedance converter 16 is A, the input voltage V1 is expressed as follows from a relationship between the input voltage V1 (voltage of the input terminal 21) and the output voltage V2 (voltage of the output terminal 22).

$$V1 = (1/A) \cdot V2 \quad \text{(Expression 2)}$$

When the electric current that flows from the capacitor 15 towards the capacitor 17 is i, all of the electric current i is sent to the capacitor 17 because the input impedance of the impedance converter 16 is extremely high. Therefore, the electric current i becomes jωC·V1. The voltage Vout of the detection signal output from the signal output terminal 20 is expressed as follows:

$$Vout = i \cdot (1/j\omega Cf) + V1 \quad \text{(Expression 3)}$$
$$= (1 + Cs/Cf) \cdot V1$$

When V2 is deleted from the above expressions 1 and 2, the following expression is obtained.

$$V1 = -(R2/R1) \cdot (Vin/A) \quad \text{(Expression 4)}$$

When this V1 is assigned to the above expression 3, the following expression is obtained.

$$Vout = -(1+Cs/Cf) \cdot (R2/R1) \cdot (Vin/A) \quad \text{(Expression 5)}$$

As clarified from this expression 5, the voltage Vout of the detection signal output from the signal output terminal 20 of the electrostatic capacitance detection circuit 10 becomes a value that depends on the capacitance Cs of the capacitor 17. Therefore, the capacitance Cs can be determined by executing various signal processing to this voltage Vout. Also, as seen in this expression 5 where the angular frequency ω is not included, the voltage Vout of this detection signal does not depend on a fluctuation in a frequency of the AC signal Vin from the AC voltage generator 11 and in a frequency of the capacitor to be detected. So, the electrostatic capacitance detection circuit (that does not have a frequency-dependent characteristic in the circuit) capable of detecting the capacitance of the capacitor 17 is realized without depending on the frequency of the AC voltage applied to the capacitor 17. Therefore, for the capacitor 17, of which capacitance value is changed at a certain frequency (sound band), such as a capacitor microphone, it is possible to specify a capacitance value directly from the voltage value thereof instead of correcting the frequency for the detected signal.

Here, when the impedance converter 16 is a voltage follower, the voltage gain becomes A=1, and both of the input terminals of the voltage follower are in an imaginary short status. So the voltage of the inverting input and the output is decided, and the voltage of the non-inverting input of the voltage follower is determined. In this case, it can be said that the operational amplifier 14 and the voltage follower are divided into an amplifier for obtaining enough gains and an amplifier for deciding the voltage. In this way, it becomes possible to connect the non-inverting input of the operational amplifier 14 to the specific potential, to improve stability of the operation, and to reduce operational errors radically while getting enough gains, which are considered to be a preferable style.

Also, in the electrostatic capacitance detection circuit 10 according to this embodiment, the operational amplifier 14, which supplies the electric current to the capacitor 15 and the capacitor 17, has the non-inverting input terminal connected to specific potential and fixed. Therefore, unlike the operational amplifier 95 in the conventional circuit shown in FIG. 1, the operational amplifier 14 can reduce operational errors and supply stable electric current with less noises to the capacitor 15 and the capacitor 17 without depending on the frequency of the input AC signal or the like, and very small capacitance of the capacitor 17 can be detected.

Figure 3A:
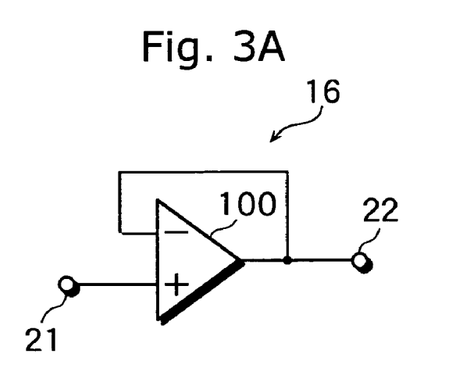
FIG. 3A through E are diagrams showing examples of an impedance converter usable in the present invention.

FIG. 3A through E show specific circuit examples of the impedance converter 16 in the electrostatic capacitance detection circuit 10 shown in FIG. 2. FIG. 3A shows a voltage follower using an operational amplifier 100. An inverting input terminal and an output terminal of the operational amplifier 100 are short-circuited. When a non-inverting input terminal of this operational amplifier 100 is an input of the impedance converter 16, and the output terminal of the operational amplifier 100 is an output of the impedance converter 16, the impedance converter 16 of which input impedance is extremely high and voltage gain A is 1 can be obtained.

Figure 3B:
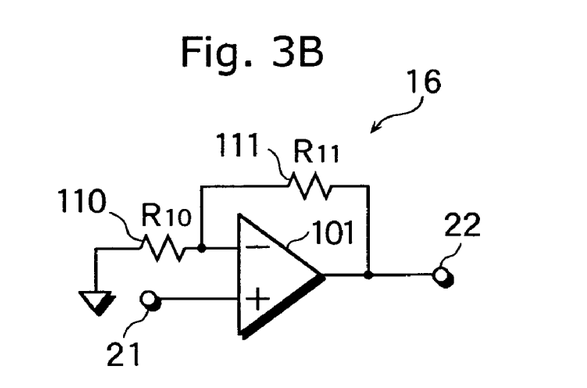

FIG. 3B shows a non-inverting amplifier circuit using an operational amplifier 101. A resistance (R10) 110 is connected between an inverting input terminal of the operational amplifier 101 and a ground, and a feedback resistance (a resistance (R11) 33) is connected between the inverting input terminal and an output terminal of the operational amplifier 101. When a non-inverting input terminal of this operational amplifier 101 is an input of the impedance converter 16, and the output terminal of the operational amplifier 101 is an output of the impedance converter 16, the impedance converter 16 of which input impedance is extremely high and voltage gain A is (R10+R11)/R10 can be obtained.

Figure 3C:
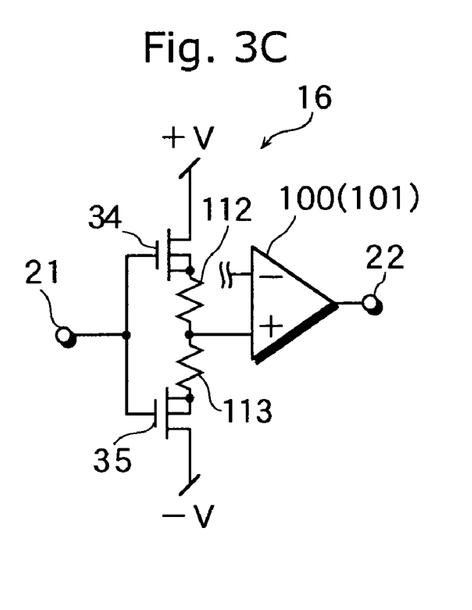

FIG. 3C shows a circuit where a buffer of CMOS structure is added to an input side of the operational amplifier as shown in FIG. 3A or B. As illustrated in the diagram, N type MOSFWT34 and P type MOSFET35 are connected between positive and negative power supplies in series via the resistance 112 and 113, and an output of the buffer is connected to an input of the operational amplifier 100 (or 101). When the input of this buffer is an output of the impedance converter 16, and the output terminal of the operational amplifier is an output of the impedance converter 16, the impedance converter 16 of which impedance is extremely high can be obtained.

Figure 3D:
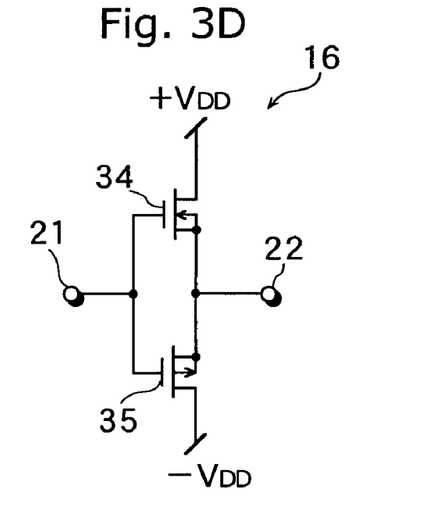

FIG. 3D shows a circuit like the buffer at the input side in FIG. 3C. As shown in the diagram, N type MOSFET34 and P type MOSFET 35 are connected between positive and negative power supplies are connected in series, and outputs are made from connection points of both MOSFET.

Figure 3E:
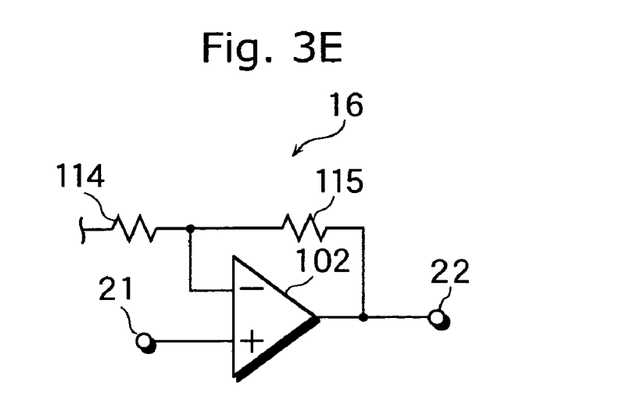

FIG. 3E is a circuit where a non-inverting input of an operational amplifier 102 is an input of the impedance converter, an inverting input terminal of the operational amplifier 102 is connected to one end of a resistance 114, and an output and the inverting input of the operational amplifier 102 are connected via a resistance 115. As indicated in FIGS. 3D and E, having these types of structure realizes the impedance converter 16 of which input impedance is extremely high.

(Second Embodiment)

Next, the following describes an electrostatic capacitance detection circuit according to a second embodiment of the present invention.

Figure 4:
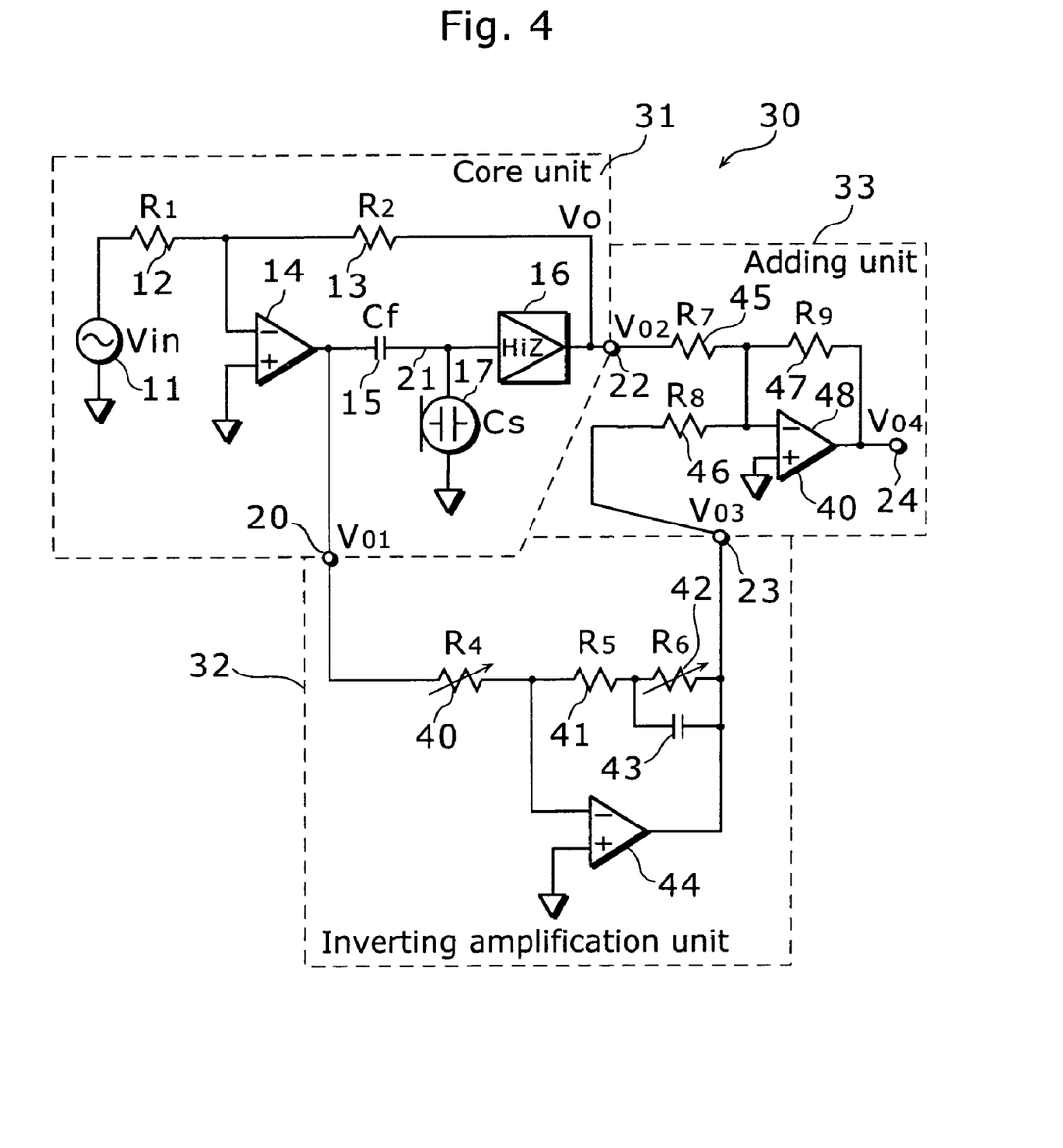
FIG. 4 is a circuit diagram of an electrostatic capacitance detection circuit according to a second embodiment of the present invention.

FIG. 4 is a circuit diagram of an electrostatic capacitance detection circuit 30 as an impedance detection circuit in the second embodiment. This electrostatic capacitance detection circuit 30 is roughly composed of a core unit 31 that is equivalent to the electrostatic capacitance detection circuit 10 as the impedance detection circuit shown in FIG. 2, an inverting unit 32 that receives signal voltage V01 at a signal output terminal 20 of the core unit 31 as an input and inverts the signal voltage V01, an adding unit 33 that adds up signal voltage V03 at an output terminal 23 of the inverting unit 32 and signal voltage V02 at an AC output terminal 22 of the core unit 31 and outputs a detection signal of voltage V04 to an output terminal 24.

The core unit 31 has the same circuit as the electrostatic capacitance detection circuit 10 shown in FIG. 2. Therefore, according to the above expression 5, the voltage V01 of the signal output terminal 20 of the core unit 31 is as follows:

$$V01 = -(1+Cs/Cf) \cdot (R2/R1) \cdot (Vin/A) \quad \text{(Expression 6)}$$

According to the above expression 1, the voltage V02 of the AC output terminal 22 of the core unit 31 is as follows:

$$V02 = -(R2/R1) \cdot (Vin/A) \quad \text{(Expression 7)}$$

The inverting unit 32 is an inverting amplification circuit comprising a variable resistance (R4) 40, a resistance (R5) 41, a variable resistance (R6) 42, a capacitor 43 and an operational amplifier 44, of which voltage gain is −1, and resistance values of the variable resistance (R4) 40 and the variable resistance (R6) 42 are adjusted to have a phase of the signal V03 at the output terminal 23 identical to the one of the signal V02 at the AC output terminal 22 of the core unit 31. Therefore, the following relation is ideally established between the input voltage V01 and the output voltage V03 of this inverting unit 32.

$$V03 = -V01 \quad \text{(Expression 8)}$$

The adding unit 33 is an adding device of which three resistances (R7) 45, (R8) 46 and (R9) 47 having the same resistance value are connected to an operational amplifier 48. So, the following relation is established among two input signals of the voltage V02 and the voltage V03 and the output voltage V04.

$$V04 = -(V02 + V03) \quad \text{(Expression 9)}$$

After the above expression 8 is assigned to this expression 9 and V03 is deleted, the above expressions 6 and 7 are assigned to it. Then, the following expression becomes effective.

$$V04 = V01 - V02 \quad \text{(Expression 10)}$$
$$= -(Cs/Cf) \cdot (R2/R1) \cdot (Vin/A)$$

Accordingly, the voltage V04 of the detection signal output from the output terminal 24 of this electrostatic capacitance detection circuit 30 is in proportion to the capacitance value Cs. Therefore, unknown capacitance value Cs and a fluctuation in the capacitance can be easily specified by executing various signal processing based on this voltage V04.

As clarified from comparison between this expression 10 and the expression 5 that indicates the voltage Vout of the detection signal according to the first embodiment, unlike the first embodiment 30, the detection signal obtained by the electrostatic capacitance detection circuit 30 according to the second embodiment contains only a component being in proportion to the capacitance of the capacitor 17, and does not contain any unnecessary offset (i.e. the voltage that does not depend on the capacitor 17). Therefore, signal processing according to the second embodiment, which specifies capacitance or a fluctuation in the capacitance of the capacitor 17 from the detection signal, can be simple.

Although a case of V03=−V01 is used in this example, the present invention is not limited to this. According to a type of the capacitive sensor, the output voltage V04 can be set as follows with a case of V03=k·V01 (k is an amplification ratio of an inverting amplification unit).

$$V04 = \{k \cdot (Cs/Cf) + (k+1)\} \cdot (R2/R1) \cdot Vin$$

Although the impedance detection circuit according to the present invention has been described based on the two embodiments and the practical examples applied to a product, the present invention is not limited to these embodiments and practical examples.

Figure 5:
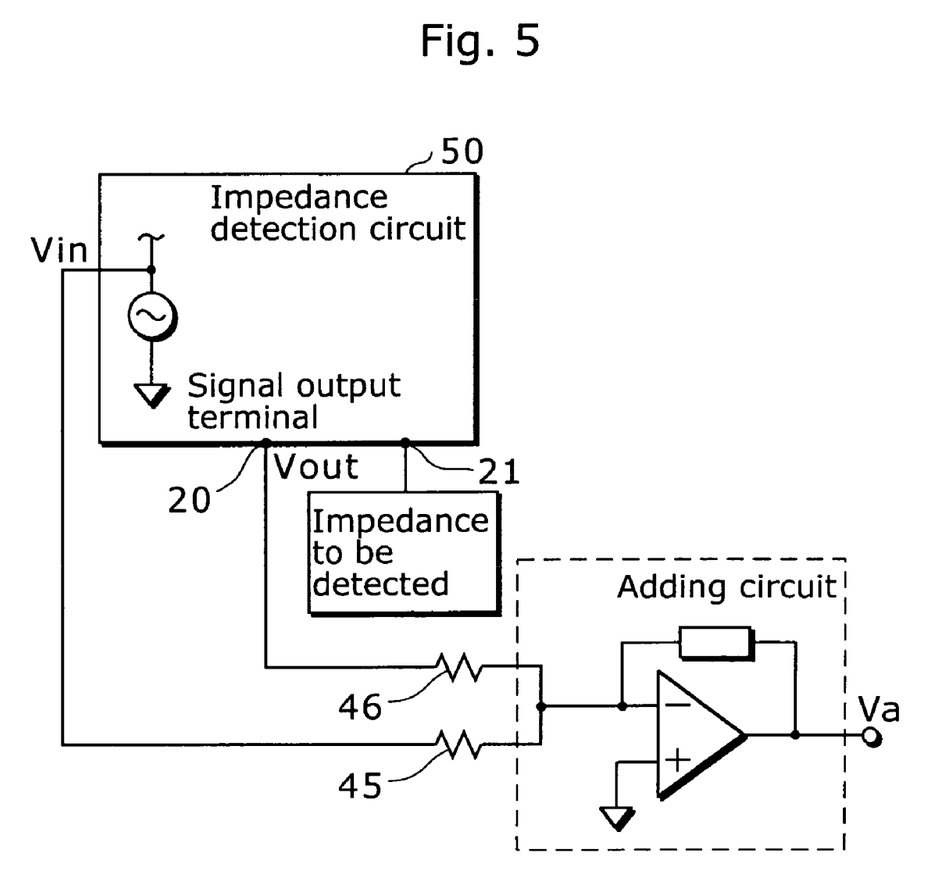
FIG. 5 shows an example that a cancellation unit of a signal corresponding to voltage generated by a voltage generator through an adding method shown in FIG. 4 is structured by another unit (an adding circuit).
Figure 6:
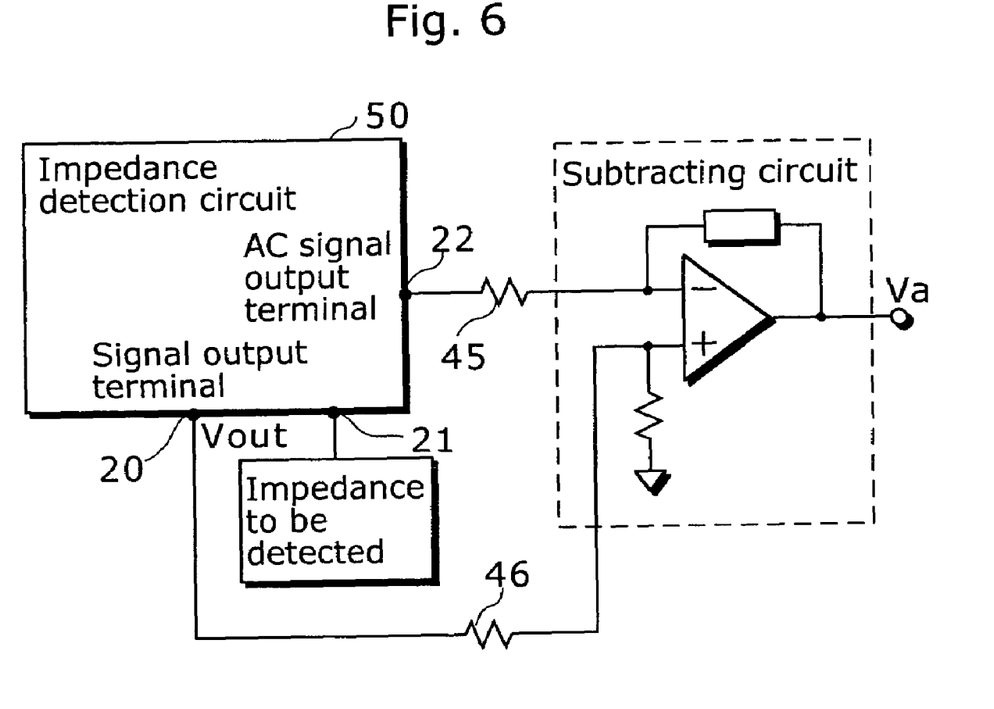
FIG. 6 shows an example that the cancellation unit of the signal corresponding to the voltage generated by the voltage generator through the adding method shown in FIG. 4 is structured by another unit (a subtracting circuit).

For instance, as shown in FIG. 5, FIG. 6 or the like, other adding unit and subtracting unit may be used for the cancellation unit of the signal corresponding to the voltage generated by the voltage generator through the adding method shown in FIG. 4.

In FIG. 5, a signal output 20 (Vout) of an impedance detection circuit 50, which is functionally identical to the electrostatic capacitance detection circuit 10, is connected to one input of the adding circuit via the resistance 46, and Vin of the impedance detection circuit 50 is connected to other input of the adding circuit via the resistance 45. Since this signal output 20 is inverted against Vin, the signal corresponding to the voltage generated by the voltage generator can be canceled by adding it. Compared with this, in FIG. 6, the output from the AC signal output terminal of the impedance detection circuit 50 and the output from the signal output terminal Vout are used as they are. Because these two signals are inverted against Vin, as shown in this diagram, the subtracting circuit becomes necessary when these signals are used as they are. The respective inputs of the adding unit and the subtracting unit are compatibly replaceable.

Moreover, for example, in the electrostatic capacitance detection circuits 10 and 30, the capacitor 15 is connected between the operational amplifier 14 and the impedance converter 16 to detect the electric current that flows to the capacitor 17. But, instead of it, an impedance element such as a resistance or an inductance may be connected. For example, when a resistance of a resistance value R3 is connected in stead of the capacitor 15, the voltage Vout of the detection signal that is output from the output terminal 20 of the electrostatic capacitance detection circuit 10 becomes as follows in stead of the above expression 5.

$$Vout = V01 \quad \text{(Expression 11)}$$
$$= \{(1 + R3 \cdot \Delta Cs \cdot \omega c \cdot \cos(\omega c \cdot t))\sin(\omega in \cdot t) +$$
$$R3(Cd + \Delta Cs \cdot \sin(\omega c \cdot t))\omega in \cdot$$
$$\cos(\omega in \cdot t)\} \cdot (Vin/A)$$

ΔCs: for a change in the capacitance of the capacitor to be detected
ωc: a frequency of the capacitor to be detected
Cd: invariable standard capacitance of the capacitor to be detected
ωin: a frequency of the input voltage Even in this case, there is no difference in a fact that the voltage V04 of the detection signal is in proportion to the capacitance value Cs. Accordingly, an unknown capacitance value Cs and the change in the capacitance can be easily specified by executing various signal processing based on this voltage V04.

Figure 7:
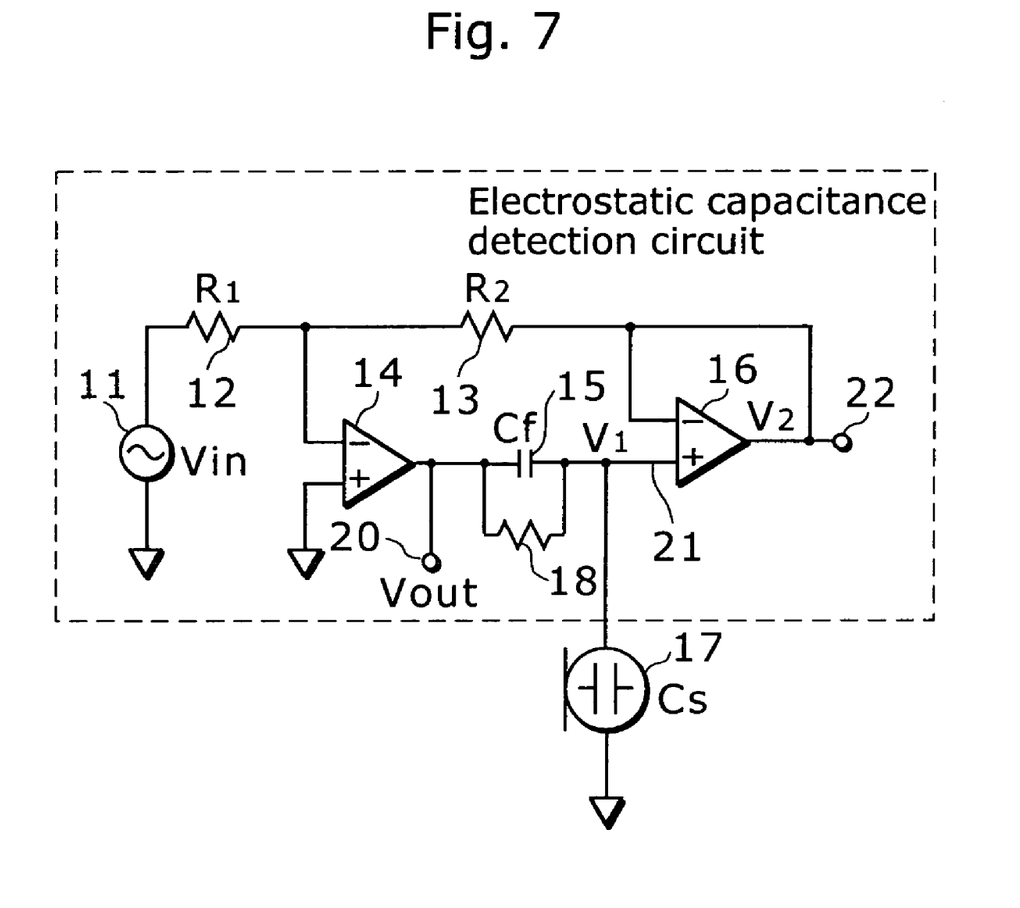
FIG. 7 is a circuit diagram of the electrostatic capacitance detection circuit according to other embodiment of the present invention.

Also, as shown in FIG. 7, a resistance 18 may be added and connected in parallel with the capacitor 15 in the electrostatic capacitance detection circuits 10 and 30 according to the above embodiments. In this way, a connecting point for the capacitor 15 and the capacitor 17 is connected to the output terminal of the first operational amplifier 14 via the resistance 18, so that having a floating status through a DC form can be avoided and the potential can be fixed.

Also, those that are connected as the impedance to be connected include unknown capacitance (in a semiconductor chip, on a board wiring, on a package wiring, etc.), or all of transducers (devices), which detect various physical quantities, such as a capacitor microphone, an acceleration sensor, a seismograph, a pressure sensor, a displacement sensor, a proximity sensor, a touch sensor, an ion sensor, a humidity sensor, a raindrop sensor, a snow sensor, a thunder sensor, a placement sensor, a bad contact sensor, a configuration sensor, an endpoint detection sensor, an oscillation sensor, an ultrasonic wave sensor, an angular velocity sensor, a liquid quantity sensor, a gas sensor, an infrared rays sensor, a radiation sensor, a water gauge, a freeze sensor, a moisture meter, a vibrometer, an electrification sensor, a publicly-known capacitive type sensor like a printed circuit board inspection device, or the like.

As has been clarified from the above explanation, by applying AC voltage to the operational amplifier via the resistance and connecting the impedance to be detected to the negative feedback loop of the operational amplifier, the impedance detection circuit and the electrostatic capacitance detection circuit according to the present invention detect impedance of the impedance to be detected. That is, the capacitive impedance element is connected between the output terminal of the operational amplifier, of which non-inverting input terminal is connected to the specific potential, and the input terminal of the impedance converter, and further the impedance to be detected is connected between the input terminal of the impedance converter and the specific potential.

In this way, most of electric current sent to the impedance to be detected flows to the impedance element, so that an accurate signal corresponding to the impedance of the impedance to be detected is output to the output terminal of the operational amplifier, which makes it possible to detect very small impedance. Especially, when each of the impedance is capacitive, very small capacitance that equals to or is less than a fF order can be detected, and measurement that does not depend the frequency of the change in the capacitance to be detected becomes possible.

Then, because the non-inverting input terminal of the operational amplifier is connected to the specific potential, and the potential at one end of the input terminal is fixed, the operational amplifier is functioned steadily, the operational error is reduced, and the noise mixed in the detection signal is restrained.

Also, since the capacitive impedance element is connected between the operational amplifier and the impedance converter, detection sensitivity, which does not depend on a frequency of the AC voltage applied to the operational amplifier and on a frequency of a change in the capacitance of the impedance to be detected, is secured. Moreover, when the resistance is connected between the operational amplifier and the impedance converter, it does not cause a problem to degrade an S/N ratio due to thermal noise from the resistance.

Here, it is possible to add the inverting amplification circuit, which inverts a signal at the signal output terminal, and the adding circuit, which adds up the output signal of the impedance converter and the output signal of the inverting amplification circuit, to the said impedance detection circuit. By doing so, any unnecessary offset component contained in the output signal of the impedance detection circuit is removed, and a net signal corresponding to the impedance of the impedance to be detected can be amplified significantly.

As has been mentioned, the present invention reduces limitation for a usage environment, detects very small impedance accurately, and realizes an impedance detection circuit and an electrostatic capacitance detection circuit and the like that are suitable for miniaturization, and especially sound performance of lightweight and compact audio communication devices such as a mobile phone is rapidly improved and its practical value is extremely high.

INDUSTRIAL APPLICABILITY

The electrostatic capacitance detection circuit according to the present invention may be used as a detection circuit of a capacitance type sensor, especially as a microphone device that is equipped with compact and lightweight devices such as a mobile phone.

We claim:

1. An impedance detection circuit that outputs a detection signal corresponding to impedance of an impedance element to be detected, comprising:
    an impedance converter of which input impedance is high and output impedance is low;
    a first capacitive impedance element;
    a first operational amplifier;
    a voltage generator that applies at least AC voltage or DC voltage to the first operational amplifier; and
    a signal output terminal that is connected to an output of the first operational amplifier,
    wherein an input terminal of the impedance converter is connected to one end of the impedance element to be detected and one end of the first impedance element,
    wherein the one end of the impedance element to be detected and the input terminal of the impedance converter are connected to each other by an unshielded conductor, and
    the first impedance element and the impedance converter are included in a negative feedback loop of the first operational amplifier.

2. The impedance detection circuit according to claim 1, further comprising:
    a cancellation unit that cancels all or a part of a signal, which corresponds to voltage generated by the voltage generator, from a signal at the signal output terminal.

3. The impedance detection circuit according to claim 1, wherein the impedance element to be detected is a capacitive impedance element.

4. The impedance detection circuit according to claim 1, further comprising a resistance element connected in parallel with the first impedance element.

5. The impedance detection circuit according to claim 1, further comprising a second impedance element connected between the first operational amplifier and the voltage generator.

6. The impedance detection circuit according to claim 1, wherein the impedance converter is a voltage follower of which voltage gain is one.

* * * * *